United States Patent [19]

Wien

[11] 4,003,380
[45] Jan. 18, 1977

[54] BIPOLAR COAGULATION INSTRUMENT

[75] Inventor: Peter Wien, Freiburg, Germany

[73] Assignee: F.L. Fisher, Freiburg, Germany

[22] Filed: Aug. 29, 1975

[21] Appl. No.: 609,052

[30] Foreign Application Priority Data

Sept. 5, 1974 Germany .......................... 2442605

[52] U.S. Cl. .......................... 128/303.17; 128/321
[51] Int. Cl.$^2$ .................... A61B 17/40; A61N 3/06
[58] Field of Search ................ 128/303.17, 303.13, 128/303.14, 303.15, 303.16, 303.18, 407–409, 321

[56] References Cited

UNITED STATES PATENTS

| | | | |
|---|---|---|---|
| 1,731,069 | 10/1929 | Herman | 128/303.16 |
| 2,011,169 | 8/1935 | Wappler | 128/303.17 |
| 2,448,741 | 9/1948 | Scott et al. | 128/303.15 |
| 3,831,607 | 8/1974 | Lindemann | 128/303.17 |
| 3,858,586 | 1/1975 | Lessen | 128/303.17 |
| 3,920,021 | 11/1975 | Hiltebrandt | 128/303.17 |

FOREIGN PATENTS OR APPLICATIONS 664,359   3/1928   France ............................. 128/407

*Primary Examiner*—Robert W. Michell
*Assistant Examiner*—Lee S. Cohen
*Attorney, Agent, or Firm*—Michael J. Striker

[57] ABSTRACT

The instrument includes a pair of coagulation electrodes adapted to be connected to the terminals of a high-frequency voltage source and having spread-apart ends subjected to a biasing force tending to maintain the ends spread apart. An outer tube surrounds the coagulation electrodes. The spread-apart ends of the electrodes project outwards from inside the outer tube. The outer tube includes two handles and is shiftable relative to the electrodes by the handles at least against the ends of the electrodes and at least partly over the ends of the electrodes to press together the ends of the electrodes. The electrodes may also be rotated relative to the outer tube and the handles.

17 Claims, 4 Drawing Figures

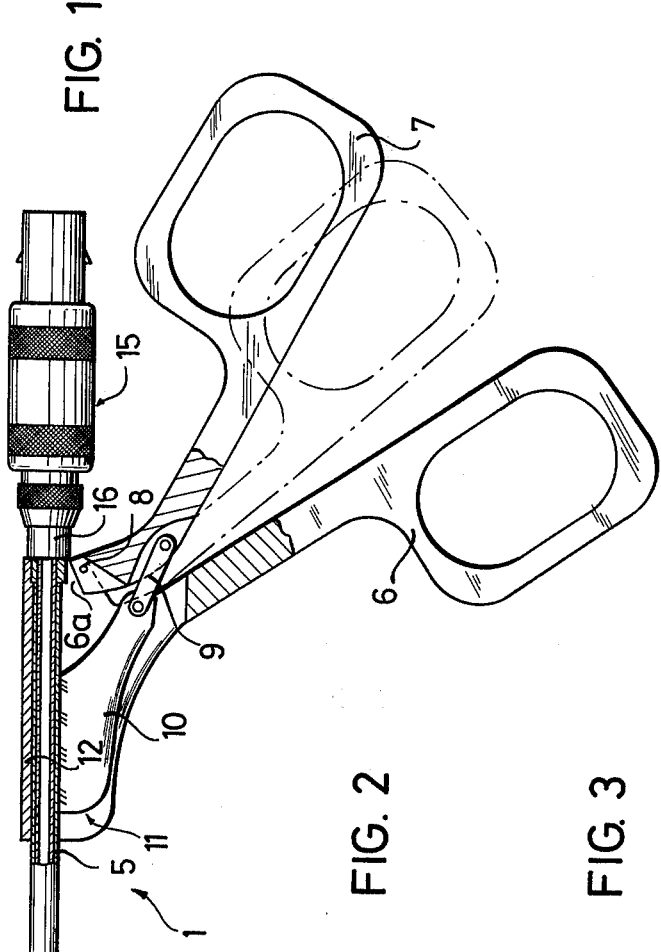
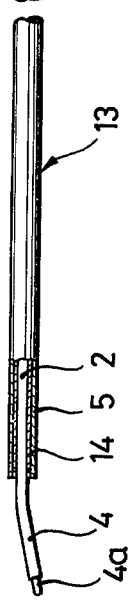
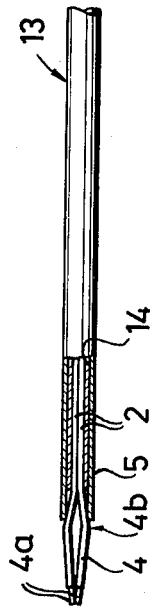
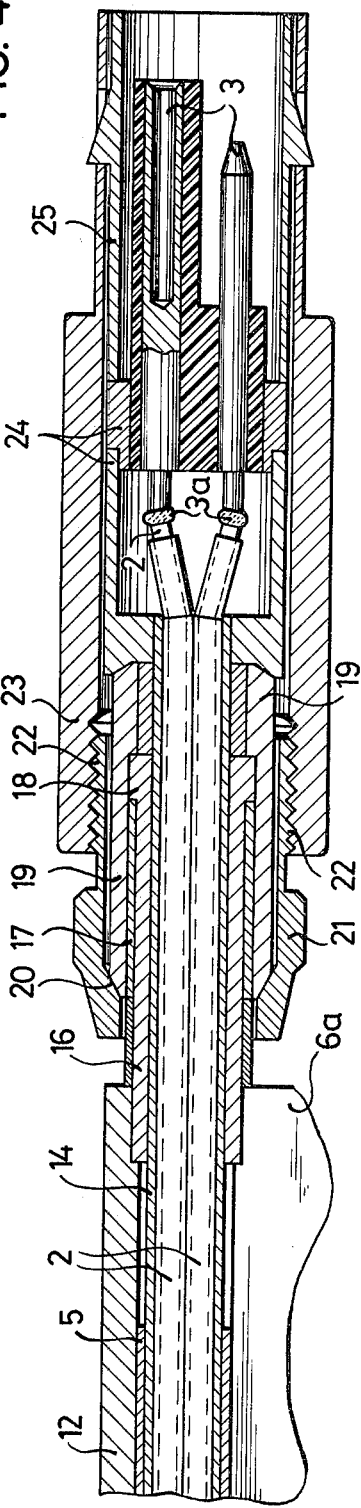

BIPOLAR COAGULATION INSTRUMENT

BACKGROUND OF THE INVENTION

The invention relates to bipolar coagulation instruments, especially microcoagulation instruments, having two coagulation electrodes across which a voltage can be established by connecting the electrodes to the terminals of a high-frequency voltage source.

Particularly in operations in deep-lying body cavities, for example laryngeal operations, coagulation probes can be disadvantages, because it can be very difficult to control in a measured way the coagulating action effected by the probe. To deal with this difficultly, bipolar coagulation tongs have been developed. However, these can be hard to manipulate properly, especially when the operating location is in deep-lying body cavity. Also, the instrument can to a very disadvantageous extent block the surgeon's view into the body cavity.

SUMMARY OF THE INVENTION

It is a general object of the invention to provide a bipolar coagulation instrument which is extremely well suited for use in deep-lying body cavities, for example in laryngeal surgery.

It is a particularly important object to so design the coagulation instrument that manipulation of the instrument of activation of the coagulating electrodes produces the least possible undesired shifting movement of the exposed electrically conductive ends of the instrument relative to the operating location.

This object and others which will become more understandable from the description, below, of a preferred embodiment, can be met, according to one advantageous concept of the invention, by making use of coagulation electrodes which are insulated from each other except at their exposed ends and which are spread apart under the action of a biasing force tending to maintain the exposed ends spread apart, with the electrodes being arranged in an outer tube with their spread-apart ends projecting out of the outer tube. The electrodes and the outer tube are movable relative to each other, and the outer tube is shiftable in direction towards the electrode ends at least against these ends and at least partly over these ends, for effecting a pressing together of the exposed electrode ends.

In this way, when the electrode ends are pressed together as a result of forwards shifting of the outer tube, the electrodes need not perform any other movement relative to the operating location. Also, the combination of the aforementioned features makes it possible to give the instrument a long and slim shape, which is advantageous for insertion into deep-lying body cavities. Despite the large distance between the operating location and the activating means manipulated by the surgeon, it is possible to achieve a reliable coagulation, with all the usual advantages of bipolar coagulation.

Advantageously, the inner diameter of the outer tube is smaller than the outer distance between the spread-apart ends of the electrodes. The shifting of the outer tube over these spread ends reliably causes the ends to be pressed together for performing a coagulation Advantageously, the instrument is provided with two handles which are mounted for swinging or pivoting movement relative to each other. One handle is connected with the electrodes or with the holding structure therefor; the other is connected with the shiftable outer tube. This results in a particularly comfortable manipulation of the instrument; one handle which is connected to the holding structure for the electrodes can be held motionless, to position the coagulation instrument as a whole, whereas the second handle can be swung for effecting the aforedescribed shifting of the outer tube.

Advantageously, the instrument has two handles like the handles of a scissors or shears, with the handle which is located more forwardly, i.e., closer to the exposed ends of the electrodes, being connected to the electrodes or the holding structure therefor, with the second handle being pivotably connected to the first, and with the second handle being connected via a linkage arm or the like, preferably through a shifting element or the like, to the outer tube for transmitting shifting movement to the latter. Then, a forwards swinging of the more rearward of the handles causes the outer tube to shift forwards against the spread-apart electrode ends, causing the electrode ends to be pressed together.

The electrodes are advantageously wire electrodes provided with shrunk-tube insulation, and are preferably silver wire. This makes for particularly good conduction to the exposed electrode tips. Nevertheless, the electrodes can be located very close to each other, which is desirable if the instrument as a whole is to be slim.

According to a preferred concept, the electrodes with their insulation can be at least partly surrounded by a guide tube or other such sleeve which ends short of the spread-apart electrode ends, with the outer tube surrounding and being shiftable along the guide tube. This prevents the shifting of the outer tube for the purpose of closing the electrode tips from damaging the insulation of the electrodes.

The visibility of the operating zone is improved if the ends of the electrodes are bent down relative to the general direction of the outer tube and the sections of the electrodes accommodated within the outer tube.

It is also advantageous if the coagulation electrodes are mounted rotatable relative to the outer tube and the handles. In this way, and in combination with the features mentioned above, it becomes possible to bring the electrodes into the best possible orientation for each operating situation without the surgeon having to change the orientation with which he holds the proximal end of the instrument. With instruments of other design the surgeon must rotate his end of the instrument to effect corresponding rotation of the coagulation electrodes, and this can lead to very considerable manipulative difficulties.

In this way the electrodes together with the guide tube accommodating the electrodes can be rotated within the outer tube, and the rotation control knob can be connected to a projection at the rear end of the instrument, which likewise facilitates the surgeon's task in effecting the rotation of the electrodes.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

FIG. 1 is a side view, in partial longitudinal section, of an exemplary coagulation instrument according to the invention;

FIG. 2 is a top view, partially in section, looking down upon the front or distal end of the instrument when the electrode ends are spread apart;

FIG. 3 is a view similar to FIG. 2, with the electrode ends pressed together; and FIG. 4 is a longitudinal section, on an enlarged scale, through the rear or proximal end of the instrument, showing a rotation control knob and the end of the electrodes.

DESCRIPTION OF THE PREFERRED EMBODIMENTS

The bipolar coagulation instrument is designated in toto by reference numeral 1, and is referred to hereinafter simply as the instrument. It is designed to be especially adapted as a microcoagulation instrument for operations in deep-lying body cavities, for example in laryngeal operations. It is comprised of two coagulation electrodes 2 adapted for connection to a high-frequency voltage source. FIG. 4 shows particularly clearly the contact connector 3 at the proximal end of the instrument 1 for effecting the connection to the voltage source. Also indicated are the solder connections 3a which secure the electrodes 2 to connector contacts 3.

FIGS. 2 and 3 make clear that the electrodes 2, which are insulated from each other, are continually subjected at their ends 4 to a force which tends to spread them apart. The electrodes 2 are arranged in an outer tube 5 out of which the spread ends 4 project. The electrodes 2 and the outer tube 5 are movable relative to each other. To be able to effect pressing together of the electrode ends 4, the outer tube 5 is made longitudinally shiftable over at least a part of the electrodes 2, as shown in FIG. 3.

The inner diameter of the outer tube 5 is made smaller than the outer spacing of the spread-apart ends 4 of the electrodes 2.

Various means can be employed to subject the ends 4 of the electrodes 2 to a force which tends to spread them apart. Separate biasing means could in theory be employed. However, according to the invention, it is preferred that the ends 4 of the metallic electrodes 2 be bent to the configuration shown in FIGS. 1 and 2, and that the ends 4 of the electrodes 2 be resiliently self-biased to the spread-apart condition (FIG. 2). Thus, if the outer sheath 5 is shifted forwards, to cause the electrode ends 4 to move towards each other (FIG. 3), then when the outer sheath 5 is subsequently shifted rearwardly the resilient self-bias of the electrode ends 4 will in itself be sufficient to cause the electrode ends 4 to spread apart again and reassume to FIG. 2 position.

As shown in FIG. 1, the instrument 1 is provided with two annular handles 6 and 7 which are swingably movable relative to each other in approximately the direction of the electrodes 2. The handle 6 is connected with the electrodes 2 or with the below-described holding structure therefor, whereas the handle 7 is connected with the longitudinally shiftable outer tube 5. In use, the handle 6 and likewise the ends 4 of the electrodes 2 are maintained motionless while operating, whereas the handle 7 is swingably moved between the solid-line and dash-dot-line positions thereof shown in FIG. 1.

It will be appreciated that what is involved are two handles 6 and 7 activatable in the manner of scissors handles, with one fixedly connected with the electrodes or the holding structure therefor, and with the other mounted at the first handle 6 or at the projection 6a associated with handle 6 for swinging movement about a pin 8 and by means of a linkage arm 9 or the like engaging the outer tube 5 via a shifting element 10. The shifting element 10, connected with the outer tube 5, is guided within a slit 11 (seen in FIG. 1 in partial side view) of the handle 6.

The rear handle 7 serves for effecting the shifting of the outer tube 5. This makes for readily observable and for that reason advantageous manipulability. By means of the handle 6 the surgeon maintains the opposed electrode points 4a in the region of the location to be treated, whereas by swinging the handle 7 the surgeon effects shifting of the outer tube 5 in approximately the same direction as that in which the handle 7 is swung. This results in a simple and advantageous way in closing of the spread-apart electrode points 4a, as shown in FIG. 3, without the electrodes needing to perform any relative movement in the direction of the change of orientation.

The stationary handle 6 connected with the electrode holding structure has above the slit 11 and for effecting the guidance of the shifting element 10 a guide of circular cross-sectional configuration for the outer tube 5. In FIGS. 1 and 4, the upper part 12 of this guide is depicted.

In the illustrated embodiment, the electrodes 2 are provided with shrunk-tube insulation and are advantageously made of silver wire.

It is desirable to make the electrodes 2 as thin as possible, so that the part 13 of the instrument 1, which is the part which will be inserted into a body cavity, will be of the slimmest possible shape. On the other hand, it is important to preclude damage to or deformation of the electrodes as a result of the movement of the outer tube 5. Accordingly, the electrodes 2 together with their insulation are at least partly surrounded by a guide tube 14 or other such sheath, with the guide tube 14 ending short of the spread ends 4 of the electrodes 2. The outer tube 5 surrounds and is shiftable along the guide tube 14 for effecting the pressing together of the electrode ends 4. In this way, the electrodes 2 can extend tightly against each other within the guide tube 14 and yet in the region of their ends spread apart from each other to such an extent as to establish the distance requisite for their being compressible towards each other in the aforedescribed manner.

In the illustrated embodiment, the ends 4 of the electrodes 2 initially extend inclined away from each other (see FIG. 2) and thereafter are bent at 4b to extend at least approximately parallel to each other with a certain spacing between them. In this way, when the exposed points 4a of the electrodes are pressed together, they will be oriented approximately opposite to each other, as shown in FIG. 3.

As indicated in FIG. 1, the ends 4 of the electrodes 2 can be bent down relative to the general direction of their elongation and relative to that of the outer tube 5. This increases the surgeon's ability to see the location to be treated.

It is desirable that, when the orientation of the electrodes is to be changed in dependence upon the location to be treated, it not be necessary to turn the entire instrument 1. With this in mind, according to one advantageous concept of the invention, the coagulation electrodes 2 are rotatable relative to the outer tube 5 and the handles 6 and 7 about a longitudinal axis of the part 13. To this end, the electrodes 2 together with the guide tube 14 which accommodates them are rotatable within the outer tube 5, as a result of which a further relative movement between the electrodes and the outer tube 5 is created. The rotation adjustment knob 15 engages a member 16 which projects over the rear end of the instrument. This member 16 engages (see FIG. 4) in the part 12 or the projection 6a of the motionless handle 6 and is there advantageously soldered. The member 16 is a hollow pipe element through which (see FIG. 4) the guide tube 14 accomodating the electrodes 2 is guided.

As can be seen the shiftable outer tube 5 ends short of the member 16. At this end of the stationary handle 6 of the instrument 1, there is rotatably mounted a sleeve 17 which is engaged by a flange 18 of the member 16. The rotation control knob 15, connected with the electrodes or with the holding structure therefor, is releasably clamped onto the outer side of the rotatable sleeve 17. To effect this releasable clamp mounting of the rotation control knob 15, a collet 19, for example a sleeve provided with a longitudinal slit, can be pushed onto the rotatably mounted sleeve 17. The collet 19 when in operating position is engaged by a clamping nut 21 provided with a clamping cone 20. The clamping nut 21 has an external thread 22 which is engaged by a tightening nut 23. If the tightening nut 23, which extends forwardly over the electrode holding structure 24 with an inner sleeve 25, is tightened, then the collet 19 is pressed fast against the rotatable sleeve 17 and in that way is made fast. On account of the rotatable mounting of the sleeve 17, the rotation control knob 15 can be turned for example by engagement of the tightening nut 23. This entire holding structure is prevented from being pulled out of the instrument by the clamping force of the collet 19 upon the sleeve 17.

Assembly and disassembly, especially in the region of the rotation control knob 15, are facilitated if the clamping nut 21 can be pushed onto the member 16 with the rotatable sleeve 17 prior to inserting the electrodes 2 with their holding structure into the member 16 and into the outer tube 5, and if the electrode holding structure at its end—i.e., at its holding unit 24— has a larger diameter than corresponding to the inner diameter of the clamping unit 21 and the inner diameter of the abutment sleeve 25 inside the tightening nut 23.

To effect the assembly, first of all the nut 21 is slid onto the member 16 and the collet 19 is pushed onto the guide tube 14. Thereafter, the guide tube 14 and the electrodes 2 accommodated therein are pushed through the hollow member 16 and the outer tube 5 and then pushed forwards. Next, the collet 19 can be pushed onto the sleeve 17 and secured by means of the tightening nut 23.

Advantageously, the tightening nut 23 simultaneously accommodates the plug contacts 3 for the electrodes 2. The plug contacts 3 are electrically insulated from each other, preferably by synthetic plastic material. At this location a cable provided with a complementarily configurated socket unit can be reliably and securely connected.

Above all, the combination of the aforementioned features and expedients produces an instrument which is especially well suited for microcoagulation in deep-lying body cavities. The instrument can be activated in a very simple manner by the relative movement of the electrodes and the outer tube, and the electrodes can always be turned into the most favorable position.

It will be understood that each of the elements described above, or two or more together, may also find a useful application in other types of constructions differing from the types described above.

While the invention has been illustrated and described as embodied in a particular microcoagulation instrument, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A bipolar microcoagulation instrument comprising, in combination, a pair of microcoagulation electrodes having spread-apart ends subjected to a biasing force tending to maintain the ends spread apart; means for connecting the electrodes to the terminals of a high-frequency voltage source; an outer tube surrounding the microcoagulation electrodes, the spread-apart ends of the electrodes projecting outwards from inside the outer tube, and the outer tube being shiftable relative to the electrodes at least against the ends of the electrodes and at least partly over the ends of the electrodes to press together the ends of the electrodes; activating means including handles for thusly shifting the outer tube; and means for rotating the electrodes relative to the outer tube and the handles of the activating means.

2. The instrument defined in claim 1, wherein the inner diameter of the outer tube is less than the outer spacing of the spread-apart ends of the electrodes.

3. The instrument defined in claim 1, the instrument including holding means for holding the electrodes in place, the activating means including two handles, at least one of which is swingable relative to the other in approximately the direction of the elongation of the electrodes, one of the handles being connected with the shiftable outer tube for transmitting shifting movement to the outer tube, and the other of the handles being connected to the holding means for the electrodes.

4. The instrument defined claim 3, the instrument having a distal end at which the spread-apart ends of the electrodes are located and also having a proximal end, the microcoagulation electrodes being provided with insulation insulating them from other proximally of the ends thereof, and further including a guide tube surrounding the two microcoagulation electrodes and extending along the length of the electrodes but ending proximally of the ends thereof, the outer tube surrounding the guide tube and being shiftable by the activating means along the latter for effecting pressing together of the ends of the electrodes, further including a member which surrounds the guide tube and the electrodes accommodated therein at the proximal end of the instrument and is connected to the guide tube non-rotatable relative to the guide tube, the means for rotating including a rotation control knob connected to the member for effecting rotation of the member.

5. The instrument defined in claim 3, the instrument further including an intermediate shifting element and a linkage arm, wherein the one of the handles which is connected with the shiftable outer tube for transmitting shifting movement to the outer tube is connected thereto via the intermediate shifting element and is swingably connected to the outer handle by means of the linkage arm.

6. The instrument defined in claim 5, wherein the one of the handles which is connected to the holding means is comprised of a portion having a guide slit, and wherein the shifting element is mounted for guided shifting movement within the guide slit.

7. The instrument defined in claim 6, wherein the portion of the handle having the guide slit is located above the guide slit and is of generally round transverse cross-sectional configuration and surrounds and guides the outer tube.

8. The instrument defined in claim 3, the instrument having a distal end at which the spread-apart ends of the electrodes are located and also having a proximal end, wherein the one of the handles which is connected with the shiftable outer tube for transmitting movement to the outer tube is the more proximal one of the handles.

9. The instrument defined in claim 1, wherein the electrodes are metal wires provided with shrunk-tube insulation covering the electrodes except at their spread-apart ends.

10. The instrument defined in claim 1, the instrument having a distal end at which the spread-apart ends of the electrodes are located and also having a proximal end, the microcoagulation electrodes being provided with insulation insulating them from each other proximally of the ends thereof, and further including a guide tube surrounding the two microcoagulation electrodes and extending along the length of the electrodes but ending proximally of the ends thereof, the outer tube surrounding the guide tube and being shiftable by the activating means along the latter for effecting pressing together of the ends of the electrodes.

11. The instrument defined in claim 18, wherein the insulated microcoagulation electrodes along the length of the guide tube and within the guide tube extend in physical but not electrical contact with each other, and wherein the ends of the microcoagulation electrodes are bent with the electrodes each extending distally of the respective bend in direction away from the other electrode to form an intermediate space through which the ends of the electrodes must move to contact each other.

12. The instrument defined in claim 11, wherein the ends of the electrodes distally of the respective bends extend at least approximately parallel to each other.

13. The instrument defined in claim 10, wherein the guide tube extends proximally of the proximal end of the outer tube, and further including a hollow sleeve member surrounding and connected to such proximal portion of the guide tube non-rotatable relative to such portion, the means for rotating including a rotation control knob connected to the hollow sleeve member with a releasable clamp action.

14. The instrument defined in claim 13, further including a collet surrounding the hollow sleeve member, a clamping nut surrounding the collet and having an internal conical clamping surface bearing upon the collet and having an external thread, and a tightening nut surrounding the clamping nut and in screwthreaded engagement with the external thread of the clamping nut.

15. The instrument defined in claim 14, wherein the clamping nut and the hollow sleeve member are configurated such that the clamping nut can be pushed onto the hollow sleeve member prior to the insertion of the electrodes into the hollow sleeve member, wherein the holding means for the electrodes at its rear end has a diameter larger than that corresponding to the internal diameter of the clamping nut and the internal diameter of the abutment inside the tightening nut.

16. The instrument defined in claim 14, wherein the means for connecting the electrodes to the terminals of a high-frequency voltage source comprises; connector contacts at the proximal ends of the electrodes, and wherein the clamping nut surrounds the connector contacts.

17. The instrument defined in claim 1, wherein the ends of the microcoagulation electrodes are bent relative to the direction of the elongation of the outer tube and of the parts of the electrodes contained within the outer tube.

* * * * *